US012674800B2

(12) United States Patent
Blake et al.

(10) Patent No.: US 12,674,800 B2
(45) Date of Patent: Jul. 7, 2026

(54) DUAL INDICATOR LIGHT PREGNANCY TESTING DEVICE

(71) Applicants: Jamond Blake, McClellanville, SC (US); Kyra Blake, McClellanville, SC (US)

(72) Inventors: Jamond Blake, McClellanville, SC (US); Kyra Blake, McClellanville, SC (US)

( * ) Notice: Subject to any disclaimer, the term of this patent is extended or adjusted under 35 U.S.C. 154(b) by 926 days.

(21) Appl. No.: 16/384,129

(22) Filed: Apr. 15, 2019

(65) Prior Publication Data

US 2020/0025756 A1 Jan. 23, 2020

Related U.S. Application Data

(63) Continuation-in-part of application No. 29/677,099, filed on Jan. 17, 2019, now Pat. No. Des. 903,897.

(60) Provisional application No. 62/699,308, filed on Jul. 17, 2018.

(51) Int. Cl.
| | |
|---|---|
| *G01N 33/543* | (2006.01) |
| *B01L 3/00* | (2006.01) |
| *G01N 33/68* | (2006.01) |
| *G01N 33/76* | (2006.01) |

(52) U.S. Cl.
CPC ...... *G01N 33/54366* (2013.01); *B01L 3/5023* (2013.01); *G01N 33/689* (2013.01); *G01N 33/76* (2013.01); *B01L 2200/087* (2013.01); *B01L 2300/027* (2013.01); *B01L 2300/08* (2013.01); *G01N 2333/59* (2013.01)

(58) Field of Classification Search
CPC ........... G01N 33/54366; G01N 33/689; G01N 33/76; G01N 2333/59; G01N 2800/36; B01L 3/5023; B01L 2200/087; B01L 2300/027; B01L 2300/08
See application file for complete search history.

(56) References Cited

U.S. PATENT DOCUMENTS 5,739,041 A * 4/1998 Nazareth .............. G01N 33/558
436/518
7,489,403 B1 2/2009 Lin et al.
(Continued)

FOREIGN PATENT DOCUMENTS

AT 512119 A1 * 5/2013
WO WO-2017071728 A1 * 5/2017 ......... G01N 21/8483

*Primary Examiner* — Elizabeth A Robinson
*Assistant Examiner* — Sophia Y Lyle
(74) *Attorney, Agent, or Firm* — Boudwin Intellectual Property Law, LLC; Daniel Boudwin

(57) ABSTRACT

A dual indicator light pregnancy testing device is provided. The pregnancy testing device includes a liquid absorbent tip disposed on a first end of a housing wherein the tip includes a channel that permits the flow of urine therethrough. A sensor is provided on an end of the channel adapted to provide a pregnancy reading when contacted with urine that has flowed through the channel disposed on the tip. A first indicator light is disposed on a housing on a second end of the pregnancy testing device and is designed to flash light of a first color when a proper amount of urine is received. A second indicator light is disposed on the housing and is designed to flash a light of a second color when the test is complete. The device is configured to provide an easy to use and accurate pregnancy test.

1 Claim, 2 Drawing Sheets

(56) References Cited

U.S. PATENT DOCUMENTS

| | | | | |
|---|---|---|---|---|
| 2004/0152208 | A1* | 8/2004 | Hutchinson | G01N 33/523 |
| | | | | 436/518 |
| 2006/0008896 | A1* | 1/2006 | Nazareth | G01N 33/689 |
| | | | | 435/287.2 |
| 2007/0292969 | A1 | 12/2007 | Canseco | |
| 2009/0305436 | A1* | 12/2009 | Plummer | G01N 33/76 |
| | | | | 436/510 |
| 2011/0287434 | A1* | 11/2011 | Menon-Johansson | ...................... |
| | | | | G01N 33/689 |
| | | | | 435/6.12 |
| 2012/0083711 | A1* | 4/2012 | Goldstein | A61B 5/4875 |
| | | | | 600/573 |
| 2012/0231552 | A1* | 9/2012 | Matallana-Kielmann | ................... |
| | | | | G01N 33/558 |
| | | | | 436/501 |
| 2014/0065033 | A1 | 3/2014 | Bae et al. | |
| 2014/0273012 | A1* | 9/2014 | Snowden | G01N 33/54366 |
| | | | | 435/7.9 |
| 2015/0094227 | A1 | 4/2015 | McCarthy et al. | |
| 2016/0011188 | A1* | 1/2016 | Anderberg | B29C 45/44 |
| | | | | 264/250 |
| 2017/0108506 | A1 | 4/2017 | Crumitie et al. | |

* cited by examiner

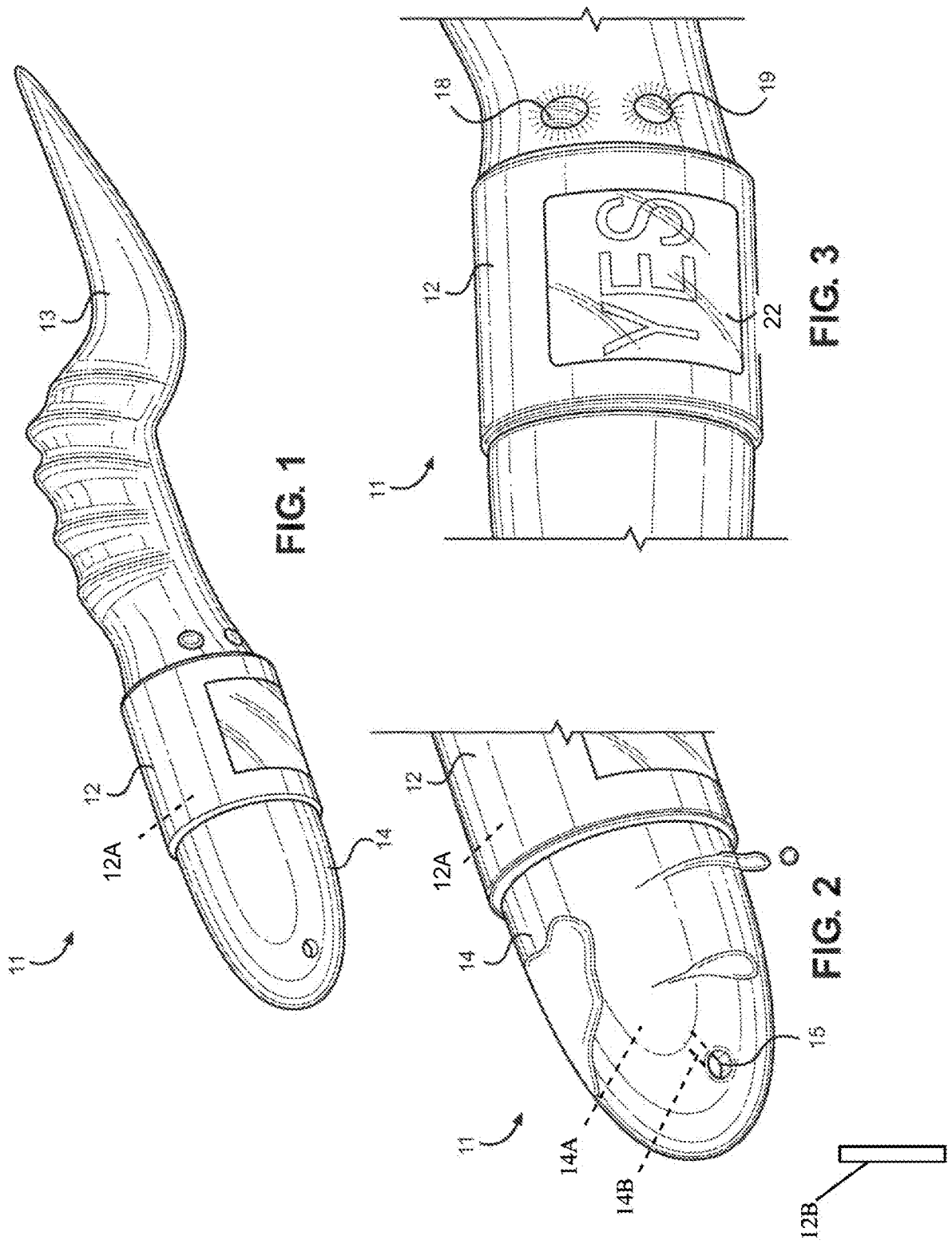

DUAL INDICATOR LIGHT PREGNANCY TESTING DEVICE

CROSS REFERENCE TO RELATED APPLICATION

This application claims the benefit of U.S. Provisional Application No. 62/699,308 filed on Jul. 17, 2018. Also, U.S. Nonprovisional application Ser. No. 29/677,099, filed on Jan. 17, 2019, is incorporated by reference herein. The above identified patent applications are herein incorporated by reference in their entirety to provide continuity of disclosure.

BACKGROUND OF THE INVENTION

The present invention relates to pregnancy testing devices. More specifically, the present invention provides a pregnancy testing device with an absorbent tip wherein a channel disposed in the tip is adapted to accept urine into the body of the device wherein a sensor disposed within a body of the device is configured to provide a pregnancy reading. Indicator lights disposed on the surface of the housing body are designed to flash a first light of a designated color when the tip has received enough urine for an accurate test, and the light on a second color from a second indicator light when the sensor has registered a reading on the pregnancy test.

Standard pregnancy tests, while effective, may be difficult and inconvenient to use. Too much urine on the stick can cause a faulty reading or take a considerable amount of time to complete. Inadequate amount of urine can yield poor or even inaccurate results from the testing. Additionally, tests may be difficult to hold while using. The process of getting the right amount of urine on the testing surface may be difficult for some people and may create a messy situation, which can be time-consuming and frustrating for the individual taking the pregnancy test. Accordingly, a device that is configured to enable an easier to use and improved pregnancy test is desired.

Devices have been disclosed in the prior art that relate to pregnancy testing devices. These include devices that have been patented and published in patent application publications. These devices include an electronic testing apparatus having a first reaction line and a second reaction line connected to a circuit board and having a light source. Other devices generally relate to pregnancy testing devices utilizing a means of testing a female subject's urine and displaying the results on an indicator. These devices, however, fail to disclose a pregnancy testing device including a first indicator light disposed on the housing configured to flash the light of a first color when a proper amount of urine is received, and a second indicator light disposed on the housing configured to flash a second color when the test is complete. Therefore, there is a need in the prior art for a new and convenient means for accurately taking and reading a pregnancy testing device.

In light of the devices disclosed in the prior art, it is submitted that the present invention substantially diverges in design elements from the prior art and consequently it is clear that there is a need in the art for an improvement to pregnancy testing devices. In this regard the instant invention substantially fulfills these needs.

SUMMARY OF THE INVENTION

In view of the foregoing disadvantages inherent in the known types of pregnancy tests now present in the prior art, the present invention provides a dual indicator light pregnancy testing device wherein the same can be utilized for providing convenience for a user attempting to take a hormonal pregnancy test while accurately knowing when a sufficient amount of urine has been received.

It is therefore an object of the present invention to provide a new and improved dual indicator light pregnancy testing device that has all of the advantages of the prior art and none of the disadvantages. The present system comprises a housing having a handle affixed to a first end and a testing head affixed to a second head thereon, wherein an aperture in the testing head connects to a channel leading to a reservoir containing a testing device within the body of the testing head. A power source within the interior volume of the housing is operably connected to a circuit board, the circuit board also being operably connected to a first and a second indicator light.

It is another object of the present invention to provide a dual indicator light pregnancy testing device wherein the testing device disposed within the testing head is replaceable and comprises a paper strip configured to react to the presence of hormones released during pregnancy present in the urine.

Another object of the present invention is to provide a dual indicator light pregnancy testing device wherein the first indicator light and the second indicator light comprise light emitting diodes (LEDs) and are configured to emit different colors depending on the results of the testing device.

Yet another object of the present invention is to provide a dual indicator light pregnancy testing device wherein the handle affixed to the first end of the housing is shaped to look like the tail of a sperm cell and have grooves adapted to receive the hand of a user, while the testing head affixed to the second end of the housing is conical shaped to resemble the head of a sperm cell.

Another object of the present invention is to provide a dual indicator light pregnancy testing device wherein a display screen is disposed on the surface of the housing and operably connected to circuit board and testing device and configured to display the results of a completed pregnancy test.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

FIG. 1 shows a perspective view of an embodiment of the dual indicator light pregnancy testing device.

FIG. 2 shows a perspective view of the testing head of an embodiment of the dual indicator light pregnancy testing device, FIG. 3 shows a perspective view of the housing of an embodiment of the dual indicator light pregnancy testing device.

DETAILED DESCRIPTION OF THE INVENTION

Figure 4:
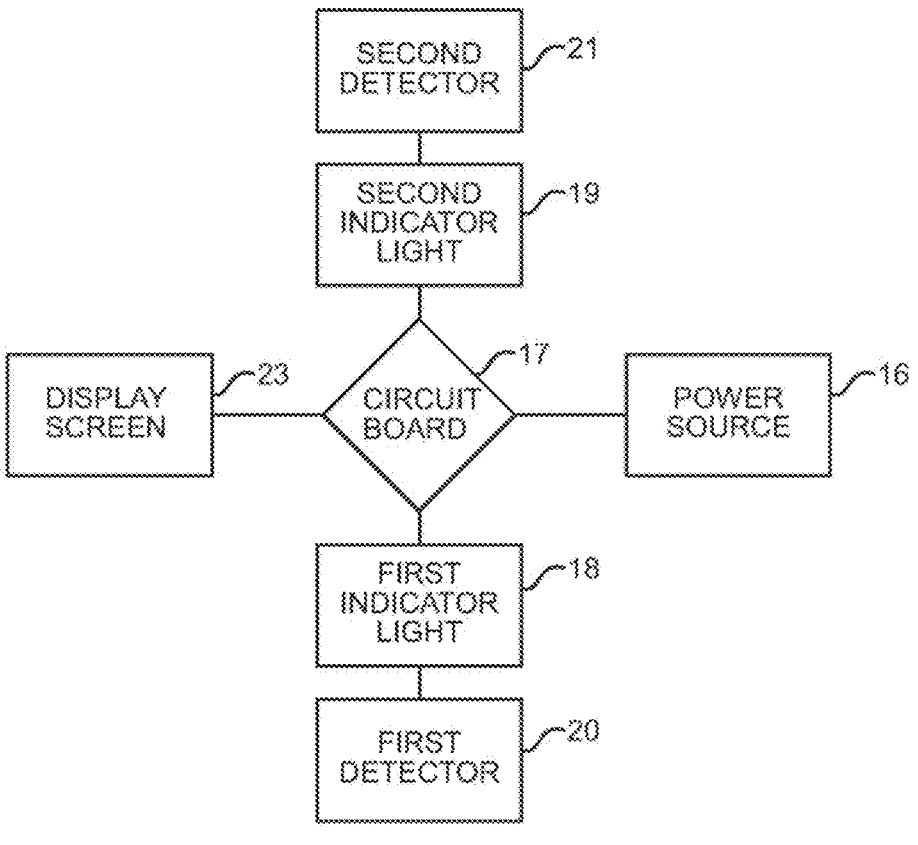
FIG. 4 shows a diagram of the electronic components of an embodiment of the dual indicator light pregnancy testing device.

Reference is made herein to the attached drawings. Like reference numerals are used throughout the drawings to depict like or similar elements of the dual indicator light pregnancy testing device. For the purposes of presenting a brief and clear description of the present invention, the preferred embodiment will be discussed as used for accurately taking a pregnancy test while indicating when a sufficient amount of urine is received for testing. The figures are intended for representative purposes only and should not be considered to be limiting in any respect.

Referring now to FIGS. 1 and 2, there is shown a perspective view of an embodiment of the dual indicator light pregnancy testing device 11 and a perspective view of the testing head 14 of an embodiment of the dual indicator light pregnancy testing device 11, respectively. The dual indicator light pregnancy testing device 11 comprises a housing 12 containing an interior volume 12A having a first end and a second end wherein an elongated handle 13 is affixed to the first end and a testing head 14 is affixed to the second end thereof. The testing head 14 of the dual indicator light pregnancy testing device 11 is conical shaped to resemble the head of a sperm cell. An aperture 15 is disposed on a surface of the testing head 14. The aperture 15 is connected to a reservoir 14A contained within the testing head 14 via a channel 14B which allows fluid to pass through the aperture 15 and into the reservoir 14A. A testing device (not shown) is disposed within the reservoir 14A located in the testing head 14 which is operably connect to a circuit board 17 contained within the housing 12. In one embodiment of the dual indicator light pregnancy testing device 11, the testing device (not shown) within the housing 12 comprises a paper strip 12B containing a substance configured to react to the presence of hormones identified as correlating with pregnancy, such as the human chorionic gonadotropin (HCG) hormone. In practice, a user will urinate on the testing head 14 which allows the reservoir 14A to fill, via fluid communication through the aperture 15 and the channel 14B, to allow for the performance of an accurate test.

Referring now to FIGS. 3 and 4, there is shown a perspective view of the housing of an embodiment of the dual indicator light pregnancy testing device and a diagram of the electronic components of an embodiment of the dual indicator light pregnancy testing device, respectively. The housing 12 comprises an enclosed space having an interior volume. A power source 16 which is operably attached to a circuit board 17 is disposed within the interior volume of the housing 12. In one embodiment of the dual indicator light pregnancy testing device 11, the power source 16 disposed within the housing 12 is comprised of a replaceable battery.

A first and a second indicator light 18 and 19 are disposed on a surface of the housing 12 and operably attached to the circuit board 17. In the illustrated embodiment, the indicator lights 18 and 19 are light emitting diodes (LEDs). The first indicator light 18 is also attached to a first detector 20 disposed within the reservoir and configured to illuminate when a sufficient amount of urine is received within the reservoir to provide an accurate test The second indicator light 19 is attached to a second detector 21 disposed on the testing device and configured to illuminate when a pregnancy testing has been completed. A display screen 22 is disposed on the surface of the housing 12 next to the first and second indicator lights 18 and 19 and operable connected to the circuit board 17. The display screen 22 is configured to display the results of the pregnancy test via indicia for a user to read in a clear and unambiguous manner. In an alternate embodiment, the second indicator light 19 is configured illuminate different color lights to signify the results of the testing device, such as green for positive and red for negative or inconclusive. The display screen 22 may also display the word "YES" with the green color light for positive testing results.

Figure 5:
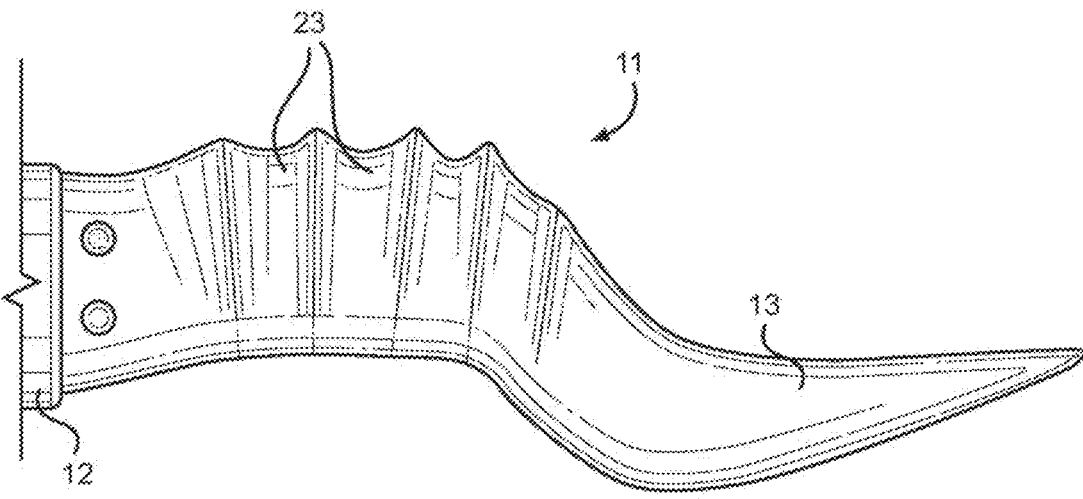
FIG. 5 shows a perspective view of the affixed handle of an embodiment of the dual indicator light pregnancy testing device.

Referring now to FIG. 5, there is shown a perspective view of the affixed handle of an embodiment of the dual indicator light pregnancy testing device. An elongated handle 13 is affixed to a first end of the housing 12. In the illustrated embodiment, the handle 13 is curved and shaped to resemble the tail of a sperm cell. A portion of the handle 13 closest to the housing 12 has an arcuate shape wherein grooves 23 along the handle 13 are adapted to receive the hand of a user in an ergonomic fashion. In alternate embodiments of the dual indicator light pregnancy testing device 11, the handle 13 may be of elongate shape having a rectangular cross-section.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A dual indicator light pregnancy testing device, consisting of:

a housing consisting of a first end, a second end, a front face, an interior volume, and a central portion;

an elongated handle affixed to the first end of the housing;

wherein the elongated handle affixed to the first end of the housing is shaped to resemble the tail of a sperm cell;

wherein the elongated handle has an arcuate portion consisting of ergonomic grooves adapted to receive a hand of a user while being handled;

further wherein the elongated handle terminates at a point;

a testing head affixed to the second end of the housing;

wherein the testing head affixed to the second end of the housing is conical shaped to resemble the head of the sperm cell;

an aperture disposed on a surface of the testing head leading to an internal channel connecting the aperture with a reservoir contained within the testing head;

a paper strip device contained within the reservoir;

wherein the paper strip disposed within the testing head is replaceable for multiple uses;

wherein the front face of the housing is perpendicular to a direction of a curvature of each of an arcuate proximal portion and an arcuate distal portion of the arcuate portion of the elongated handle;

a power source operably connected to a circuit board disposed within the interior volume of the housing;

further wherein the curvature of the arcuate proximal portion is disposed opposite of the curvature of the arcuate distal portion;

wherein the power source disposed within the housing consists of a battery;

the paper strip is adapted to chemically react when encountering human chorionic gonadotropin (HCG) hormone, a hormone identified as correlating with pregnancy;

a first indicator light operably connected to the circuit board;

a first detector disposed within the reservoir and configured to illuminate the first indicator light when a sufficient amount of urine is received within the reservoir;

a second indicator light operably attached to the circuit board;

wherein the first indicator light and the second indicator light consist of light emitting diodes (LEDs);

wherein the second indicator light is configured to emit a color depending on the reading provided by the paper strip;

a second detector disposed on the paper strip and configured to illuminate the second indicator light when testing has been completed;

wherein the second indicator light illuminates a green color for positive results and a red color for negative results or inconclusive results;

a display screen disposed on the central portion of the housing;

wherein the display screen displays "YES" with the green color light for positive results;

wherein the central portion is disposed between the testing head and the elongated handle;

wherein the central portion consists of a diameter greater than a diameter of each of the testing head and the elongated handle; and wherein the display screen is operably connected to the circuit board and the paper strip and is configured to display results of a completed pregnancy test;

wherein the aperture in the testing head connects to the internal channel leading to the reservoir containing the paper strip within the body of the testing head;

wherein the aperture is connected to the reservoir contained within the testing head via the channel which allows fluid to pass through the aperture and into the reservoir; and wherein the user will urinate on the testing head which allows the reservoir to fill, via fluid communication through the aperture and the channel, to allow for an accurate performance of the test.

\* \* \* \* \*